(12) United States Patent
Steen

(10) Patent No.: US 6,794,124 B2
(45) Date of Patent: Sep. 21, 2004

(54) PRESERVATION SOLUTION

(75) Inventor: Stig Steen, Lund (SE)

(73) Assignee: Stiftelsen Facthor, Lund (SE)

( * ) Notice: Subject to any disclaimer, the term of this patent is extended or adjusted under 35 U.S.C. 154(b) by 0 days.

(21) Appl. No.: 09/484,048

(22) Filed: Jan. 18, 2000

(65) Prior Publication Data

US 2002/0102720 A1 Aug. 1, 2002

Related U.S. Application Data

(63) Continuation-in-part of application No. 09/093,614, filed on Jun. 9, 1998, now abandoned.

(30) Foreign Application Priority Data

Dec. 15, 1995 (SE) ............................................... 9504505

(51) Int. Cl.$^7$ .............................. A01N 1/00; A01N 1/02
(52) U.S. Cl. ........................... 435/1.1; 435/1.2; 435/1.3
(58) Field of Search ........................... 435/1.1, 1.2, 1.3

(56) References Cited

U.S. PATENT DOCUMENTS

| | | | |
|---|---|---|---|
| 5,082,831 A | 1/1992 | Leaf et al. ..................... | 514/56 |
| 5,145,771 A | 9/1992 | Lemasters et al. ............. | 435/1 |
| 5,370,989 A | 12/1994 | Stern .............................. | 435/1 |
| 5,407,428 A | 4/1995 | Segall et al. | |
| 6,150,409 A | * 11/2000 | Restrepo et al. ............ | 514/535 |

FOREIGN PATENT DOCUMENTS

| | | |
|---|---|---|
| DE | 37 05 874 | 9/1988 |
| EP | 0 580 444 | 1/1994 |
| RU | 1836905 A | 8/1993 |
| WO | 92/18136 | 10/1992 |
| WO | WO 96/19918 | 7/1996 |

OTHER PUBLICATIONS

DIFCO Manual, 10th Edition, p. 1136, 1984.*
Pinsky et al., "Cardiac Preservation is Enhanced in a Heterotopic Rat Transplant Model by supplementing the Nitric Oxide Pathway" J. Clinical Invest. 93: 2291–97 (1994).
Bical et al., "Aortocoronary bypass with homologous saphenous vein: long–term results" Ann. Thoracic Surgery 30 (6): 550–7 (1980).
Colt "A solution to preserve the intima when vein grafts are irrigated and/or preserved" Vascular Surgery 11(2):61–2 (1977).
Ingemansson et al., "Perfadex is superior to Euro–Collins solution regarding 24 hour preservation of vascular function" Ann. Thoracic Surgery 60 (5): 1210–4 (1995).

Nozick et al., "Autogenous vein graft throumbosis following exposure to calcium–free solutions", J. Vardiovasc. Surgery 23(2): 166–73 (1981).
Naka et al., "Nitroglycerin maintain graft vascular homeostatsis and enhances preservation in an orthotopic rat lung transplant model" J. Thoracic and Cardiovascular Surgery 109(2):206–10 (1995).
Hisatomi et al, Benficial effect of thje addition of nitroglycerin to the cardioplegic solution on the cold–stored reperfused isolated rat heart Japan. Circulation Journal 57 (6): 558–62 (1993).
Ingemansson et al., "Importance of calcium in long–term preservation of the vasculature" Ann. Thoracic Surgery 61(4): 1158–62 (1996).
STN International, File HCAPLUS, HCAPLUS Accession No. 1992.503870, Mariyama, Hiroshi, "The Studies of Terminal Cardioplegic Solution with Additional Glyceryl Trinitrate (GTN) After Hypothermic Simple Immersion of Rat Heart"; & Kurume Igakkai Zasshi, (1992), 5 (2/3), 197–207.
American Journal of physiology, 1994, vol. 266, pp. H1729–H1737, Omachi et al., "Inhibition of th calcium paradox in isolated rat hearts by high perfusate sucrose concentrations".
The Journal of Thoracic and Cardiovascular Surgery, 1993, vol. 105, No. 2, pp. 353–363, Menasche et al., "Improved recovery of heart transplants with a specific kit of preservation solutions".
Pflugers Archiv, European Journal of Physiology, 1978, vol. 373, pp. 249–257, Drueke et al., "Effects of Hyperoncotic Albumin and Parathyroid Hormone Infusion on Jejunal Electrolyte and Water Absorption in the Rat".
The Annals of thoracic Surgery, May 1995, vol. 59, No. 5, pp. 1177–1181, Ingemansson et al. "Long–Term preservation of Vascular Endothelium and Smooth Muscle".
Current Eye Research, 1991, vol. 10, No. 12, pp. 1129–1136, Walkenbach et a., The effects UW solution and its components on corneal thickness during and after storage.
Cryobiology, 1989, 26, 407–412, Lindell et al., "Hypothermic perfusion or rabbit livers: effect of perfusate composition (Ca and lactobionate) on enzyme release and tissue swelling".

* cited by examiner

*Primary Examiner*—Sandra Saucier
*Assistant Examiner*—Vera Afremova

(57) ABSTRACT

An improved preservation solution is described, which is intended for the preservation of organs and tissues, or parts thereof, from humans and animals. The improved preservation solution contains calcium, at least one colloidosmotically active substance, and nitroglycerin. Also described is a method for preserving organs and tissues, or parts thereof, from humans and animals in the improved preservation solution.

14 Claims, 6 Drawing Sheets

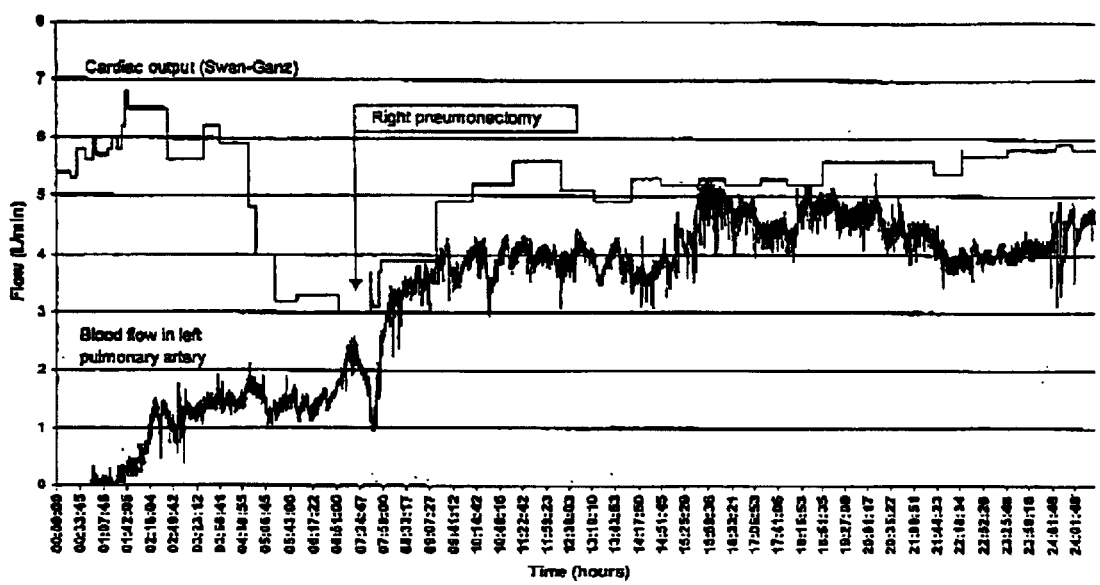

PRESERVATION SOLUTION

The present application-in-part application is a continuation of U.S. Pat. Ser. No. 09/093,614, filed June 9, 1998, incorporated by reference, now anandoned which in turn is a continuation of International Application PCT/SE96/01664, with an international filing date of Dec. 16, 1996, which in turn claims priority from Swedish application number 9504 505-0, filed 15 Dec. 1995.

FIELD OF THE INVENTION

The present invention relates to an improved preservation solution for organs and tissues, or parts thereof, from humans and animals.

BACKGROUND ART

In coronary artery surgery (about 800 operations per one million inhabitants a year) and in peripheral vascular surgery (about 100 operations per one million inhabitants a year), so-called physiological saline solution (0.9% NaCl) is in use today in most European clinics as a solution for washing away blood from blood vessel transplants, and for storing blood vessel transplants before inserting them in their new positions. In coronary artery surgery, use is generally made of the vena sapena magna, i.e. the superficial vein extending from the inside of the foot over the inner ankle and along the inside of the lower leg and the thighbone to the groin, where it joins the thigh vein (vena femoralis). In a coronary artery operation, first the vena sapena magna in one leg is removed, while the breastbone is opened and preparatory measures are taken for connection to a heart-lung machine. After removal of the vena sapena magna, this blood vessel is flushed with saline solution of the above-mentioned type, on the one hand to wash away all blood from the inside of the vessel and, on the other hand, to ensure that one has not neglected to ligate any branch of the vein, i.e. to tie the branches with a thread with a view to preventing leakage therethrough. Subsequently, the removed vein is placed in a dish containing saline solution of room temperature, i.e. 20–25° C. Then the heart-lung machine is connected and cardioplegia is given to the heart. About 15–20 cm-long segments are cut off from the vein in the dish and are sewn as a so-called aortacoronary vein bypass to the sick coronary arteries. Before all vessel transplants are sewn and the blood again circulates through these, a period of up to 2 hours may have passed. For patients who are to have one or two cardiac valves inserted as well, this period can be still longer.

Instead of storing the vessel transplants in saline solution before being sewn, some surgeons use the patient's own blood. Blood is then drawn off from the patient and is placed in a dish. The transplant is then allowed to lie in this blood before being sewn to the heart. First the temperature is 37° C. but rapidly falls to room temperature. It is thought that since blood is the medium to which the vessel is exposed throughout life, this would be the ideal storage medium for a vascular transplant.

In heart surgery, the coronary artery surgery constitutes about 70% of the operations on adults. It is well known from studying experiments on animals that when a vascular transplant is used where the endothelium is destructed, so-called intimal hyperplasia is released and the transplants are occluded after some time (the vascular lumen becomes smaller and smaller and at last the flow of blood is stopped completely). In clinical follow-up studies, it has been found that 5 years after a coronary artery operation about 30–50% of the venous transplants have been occluded, and when these are studied histologically, a pronounced intimal hyperplasia will be discovered. This thus applies to venous transplants which have been rinsed and stored in the above-mentioned physiological saline solution.

The applicant's research team has intensely studied both short-term and long-term preservation of blood vessels. Regarding short-term preservation of blood vessels, i.e. up to 2 hours preservation, it has been found that a physiological saline solution is toxic to the vascular endothelium. If a saline solution is flushed through, for example, the arteria iliaca of a rat, intimal hyperplasia can be found in the vessel after about one month. If, on the other hand, serum is used for rinsing correspondingly, no intimal hyperplasia will be discovered. Thus, the use of a physiological saline solution as preservation solution is not favourable to the blood vessels. All the same and in the absence of a better alternative, the clinical use of physiological saline solution, however, continues in most thoracic surgery centres throughout the world.

The applicant's research team has also demonstrated that blood is not satisfactory as a preservation solution. Blood of room temperature which is stored in a dish and is not oxygenated is extremely toxic to the endothelia of the blood vessels and inhibits the endothelial function to a considerable extent. This may seem to be a paradox, but since blood is an organ that has its normal function only when it is moving and is continuously oxygenated in the lungs, it cannot function in the normal manner. Deoxygenated, non-moving blood contains, like all other blood, white and red blood corpuscles and thrombocytes. Indeed, it is well known that white blood corpuscles are activated in case of hypoxaemia (low concentration of oxygen), and that they then produce toxic substances.

The applicant's research team has also confirmed that extracellular solutions can preserve blood vessels, but only for limited times, at room temperature. Extracellular solutions, in the literature sometimes misleadingly called preservation solutions, are solutions having ionic concentrations similar to plasma. The classic extracellular solution is Ringer's solution, which has a normal extracellular concentration of sodium, potassium, calcium and magnesium. To match the positive ions for obtaining ionic equivalence, chloride, lactate or acetate are used in different types of Ringer's solution. For functional in vitro studies the classical organ bath solution is Krebs solution which is electrolytically constructed like Ringer's solution. However, Krebs solution also contains glucose for metabolism, and it contains phosphate and bicarbonate buffers to achieve a pH of 7.40 when this solution is bubbled with a mixture of 95% oxygen and 5% $CO_2$ at 37° C. If a cold perfusion is preferred, enough oxygen is physically dissolved to match the lowered metabolism caused by the cooling. However, neither of these two methods have been a success for extended preservation periods in experimental transplantation. During the cooling of hypothermia, rigidity develops in the cell endothelial membranes. This occurs because the fluidity of the lipids is diminished as an effect of the temperature reduction. The rigidity of the endothelium contributes to the endothelial injury described following prolonged cold perfusion with the intention to preserve, for example, the kidney and the liver.

Extracellular solutions exhibit what has been called the "calcium paradox." If an organ is perfused with an extracellular solution without calcium for a while, and then the perfusion continues with the same solution but now including calcium, the organ may be destroyed more quickly compared to perfusing it only with the calcium free solution, i.e. perfusion without calcium is dangerous, and perfusion with calcium is dangerous—that is the paradox. In clinical organ preservation, the organ is immediately cooled down by flushing it with a cold preservation solution created, for example, for cold anaerobic storage.

It should be emphasized that the composition of preservation solutions used for cold anaerobic storage needs to be constructed in quite another way than conventional extracellular solutions. This is due in part, at least, to the effects of hypothermia.

In the first successful liver transplantation performed, Welch found that 33 minutes of warm ischemia of the dog liver was the upper limit, if the recipient animal was going to survive the operation (Goodrich E O, Welch H N, Nelson J A et al: Homotransplantation of the canine liver. Surgery 39:244, 1956. This reference is incorporated by reference herein.). With this approach, success was noted in 21 of the 49 cases, which survived for at least 5 days. Moore et al., were the first to describe the use of hypothermia in preservation of the liver, namely by surface cooling of the organ, but they did not attempt to prolong the ischemic time to more than half an hour (Moore F D, Smith L L, Bumap T K et al.: One stage homotransplantation of the liver following hepatectomy in dogs. Transplant Bull 6:103, 1959. This reference is incorporated by reference herein.). In addition to cooling the whole donor animal by immersing it in an ice bath, Starzl also used so-called core cooling of the liver by flushing out the blood through the portal vein with chilled Ringer's lactate solution (Starzl T E, Bernhard V M, Cortes N, Benvenuto R: A technique for one-stage hepatectomy in dogs. Surgery 47:880, 1959; Starzl T E, Kaupp H A, Brock D R, Lazarus R E, Johnson, R F: Reconstructive problems in canine liver homotransplantations with special reference to the postoperative role of hepatic venous flow. Surg. Gyn Obstet 111:733, 1960. These references are incorporated by reference herein.). He thereby found that cold ischemic times for up to 2 hours were compatible with survival of the recipient dog, but longer ischemic times resulted in a so-called venous outflow block, leading to the death of the recipient.

It was apparent from these and subsequent studies that hypothermia had a protective effect during ischemia, and in fact, hypothermia has become the main principle in organ preservation. For example, Calne and Pegg showed that simple cooling of ischemic kidneys with cold blood was effective for preserving the function for 12 hours (Calne R Y, Pegg D E, Pryse-Davies J, Leigh-Brown F: Renal preservation by ice-cooling, An experimental study relating to kidney transplantation from cadavers. Br MedJ 2:651, 1963. This reference is incorporated by reference herein.). By investigating recipients of paired cadaver kidneys subjected to up to 1 hour of warm ischemia, followed by up to 10 hours of cold ischemia, Bergentz et al. showed that the function was immediate after transplantation of these kidneys (Bergentz S E, Brunius U, Claes G, Gelin L E, Lewis D H: Double cadaver renal transplantations: An analysis of twenty-one pairs with special reference to the effect of variations in ischemic time, Ann Surg 170:996, 1969. This reference is incorporated by reference herein.).

Hypothermia probably exerts its protective effect during ischemia by reducing the rate of cellular metabolism. The reduction in the activity of most enzymes in normothermic animals is approximately 12- to 13-fold when the temperature is reduced from 37° C. to close to 0° C. Most organs can tolerate a warm ischemic period for 30 to 60 minutes without loss of function. Thus, it could be predicted that simple cooling of the organ could prolong the tolerance of an organ to ischemia to 6–12 hours, which in the case of the kidney is in accordance with the findings of Calne and Pegg, and for the lungs with the findings of Steen (Steen S, Sjöberg T. Ingemanson R, Lindberg L: Efficacy of topical cooling in lung preservation. Is a reappraisal due?, Ann Thorac Surg 1994; 58:1657–63. This reference is incorporated by reference herein.). Thus, cell metabolism decreases during hypothermia, and the consumption of oxygen is reduced. For example, at 5° C., the oxygen consumption in the kidney is known to be only about 5% of the value at normothermia.

Hypothermia per se has certain negative side effects resulting in the need for special preservation solutions for cold anaerobic storage. One side effect of hypothermia is an inhibition of the Na/K ATPase, causing a pronounced cell swelling during hypothermia. In fact, since the sodium pump becomes inoperative because of the cooling, swelling will occur even if sufficient ATP is present. The same degree of swelling that occurs in tissue slices incubated at 0° C., can be provoked by incubation with ouabain, an inhibitor of Na/K ATPase (D'Allesandra A, Southard J H, Kalayglou M, Belzer F O: Comparison of cold storage and perfusion of dog livers on function of tissue slices. Cryobiology 23:161, 1986. This reference is incorporated by reference herein.). Hypothermia induced cell swelling is more prominent in the heart and liver than in the kidney, because of a difference in cold sensitivity of the membrane pumps between these tissues (Martin D R, Scott D F, Downes G L, Belzer F O: Primary cause of unsuccessful liver and heart preservation: cold sensitivity of the ATPase system. Ann Surg 175:11, 1972. This reference is incorporated by reference herein.). Similar to the situation during warm ischemia, there will be a cellular loss of potassium and a gain of sodium and calcium as an effect of the inhibition of the membrane pumps.

During normal resting conditions, the intracellular $Ca^{2+}$ concentration is 1,000–10,000 times lower than that of the extracellular fluid (Kretsinger RH: The informational value of $Ca^{2+}$ in the cytosol, Adv Cyclic Nucleotide Res 11:1, 1979. This reference is incorporated by reference herein.). This large gradient is maintained by the action of the $Ca^{2+}$ sequestering system in the mitochondria and endoplasmic reticulum, as well as by the action of the Na/Ca ATPases of the endoplasmic reticulum and the cell membranes (Trump B F, Berezeky I K: Role of sodium and calcium regulation in toxic cell injury, In Mitchell J R, Horning M G, eds.: Drug metabolism and Drug toxicity, Raven Press, New York, 1984. This reference is incorporated by reference herein.). Thus, lack of ATP will lead to an increase in the cytoplasmic concentration of $Ca^{2+}$. Based on the finding that $Ca^{2+}$ accumulates in liver cells damaged by either ischemia or different hepatotoxins (Bergentz et al., id.; Trump et al. id.; Keppler D., Popper H, Bianchi L, Reutter W, eds: Mechanism of hepatocyte injury and death, MTP Press, Lancaster, England, 1984; Zimmerman H J: Hepatotxicity: The adverse effects of drugs and other chemicals on the liver, Appleton-Century-Crofts, New York, 1978; Farber J L: Calcium and the mechanisms of liver necroses, In, Popper H, Schafffner F, eds.: Progress in liver diseases, Vol. 7, Grune & Straton, New York, 1982, chap. 20. These references are incorporated by reference herein.), Farber has suggested that inflow of $Ca^{2+}$ from the extracellular fluid is a final common pathway in liver cell death (Farber, id.; Schanne F A, Kane A B, Young E E, Farber J L: Calcium dependence of toxic cell death: a final common pathway, Science 206:700, 1979; Casini A F, Farber J L: Dependence on carbon tetrachloride-induced death of cultured hepatocytes on the extracellular calcium concentration. Am J Pathol 105:138, 1981; Farber J L: The role of calcium in liver cell death, In Keppler D, Popper H, Bianchi L, Reutter W, eds: Mechanism of hepatocyte injury and death, MPT Press, Lancaster, England, 1984. These references are incorporated by reference herein.). It has also been shown that blockers of $Ca^{2+}$ entry will alleviate liver cell injury (Schanne F A, et al. id., McClean A E M, McLean E, Judah J D: Cellular necrosis in the liver induced and modified by drugs, Int Rev Exp Pathol 4:127, 1965; Landon E J, Jaiswal R K, Naukam R J, Sastry B V R: Effects of calcium channel blocking agents on membrane microviscosity and calcium in the liver of carbon tetrachloride treated rat, Biochem Pharmacol 33:3553, 1984; Fleckenstein A., Frey M, Fleckenstein-Grun G: Cellular injury by cytosolic calcium overload and its prevention by calcium antagonists—a new principle of tissue protection, In Keppler D, Popper H, Bianchi L, Reutter W, eds: Mechanism of hepatocyte injury and death, MTP Press, Lancasterm England, 1984; Lefer A M, Papanicolaou G: Beneficial action on two novel calcium channel blockers in the isolated perfused hypotoxic cat liver, Methods Findings Exp Clin Pharmacol 7:59, 1985. These references are incorporated by reference herein.). Further, calcium ionophors, i.e., compounds that facilitate $Ca^{2+}$ entry across cell membranes, have been shown to cause liver cell death (Lamb R G, Snyder J W, Coleman J B: New trends in the prevention of hepatocyte death, Modifiers of calcium movement and of membrane phospholipid metabolism, In Testa B, Perissoud D., eds.: Liver drugs: From experimental pharmacology to therapeutic application, CRC Press, Boca Raton, Fla., 1988, Chapter 4. These references are incorporated by reference herein.). As a result of these findings, organ and tissue preservation solutions created for cold anaerobic storage have always been constructed without $Ca^{2+}$.

As earlier mentioned, Starzl used cold Ringer's lactate solution, i.e. not a genuine preservation solution, to flush the liver to obtain core cooling quickly, and this allowed for 2 hours preservation in the dog liver transplantation model. Because of the relative inefficiency of this technique, however, research for several years focused on other methods for organ preservation.

However, in 1969 there was a breakthrough for preservation by simple cold storage. Collins showed that simple cold storage of the kidney for 30 hours was possible with a new type of hypertonic flushout solution, hereafter called Collins solution (Collins G M, Bravo-Shugarman M, Terasaki P I: Kidney preservation for transportation. Initial perfusion and 30 hours ice storage. Lancet 2:1219, 1969. This reference is incorporated by reference herein.). This solution came into immediate use for clinical kidney preservation, and soon became the most used solution worldwide. This solution was calcium free, and had intracellular concentrations of sodium and potassium, i.e. low sodium and high potassium concentrations.

In 1977, Collins solution was tried for preservation of the liver, and it allowed 18 hours of preservation of the canine liver (Benichou J, Halgrimson C G, Weil R III, Koep L J, Starzl T E: Canine and human liver preservation for 6 to 18 hours by cold infusion, Transplantation 24:407, 1977. This reference is incorporated by reference herein.). This solution was then adopted by Starzl's group for clinical liver preservation (Beichou et al. id.; Starzl T E, Iwatsuki S, Esquivel C O et al.: Refinements in the surgical technique of liver transplantation, Sem Liv Dis 5:349, 1985. This reference is incorporated by reference herein.), and was slightly modified to what is called Euro-collins solution (Dreikorn K, Horsch R, Rohl R: 48- to 96-hour preservation of canine kidneys by initial perfusion and hypothermic storage using the Euro-Collins solution, Eur Urol 6:221, 1980. This reference is incorporated by reference herein.), and became the most extensively used liver and kidney preservation solution until the development of the University of Wisconsin preservation solution. Since the extracellular solution Ringer's lactate allows only 2 hours and the intracellular solution Collins solution allows up to 18 hours of cold storage of the canine liver (Starzl T E, et al., Reconstructive problems . . ., id., and Levy, id.), it was obvious that the composition of the cold storage solution influences the results of preservation during cold anaerobic storage. Initially, most authors regarded the success behind Collins solution as a result of its high content of potassium (Collins G M, Hartley L C J, Clunie G J A: Kidney preservation for transportation. Experimental analysis of optimal perfusate composition. Br J Surg 59:187, 1972; Collins G M, Halasz N A: Forty-eight hour ice storage of kidneys: Importance of cation content. Surgery 79:432, 1976; Jensen E H: Preservation of rabbit kidneys without perfusion. The significance of the Na+/K+ ratio; the phosphate concentration and the dextrose concentration in the washout fluid. In Pegg D E, ed.: Organ preservation. Churchill Livingstone, Edinburgh and London, 1973, pp. 7–15. The cited portions of these references are incorporated by reference herein.). It was assumed that the intracellular composition of this solution was saving high energy phosphate by decreasing the load of the cell membrane pumps (Collins, Halasz, et al., id.). In the early studies it was also assumed that the high content of magnesium was important for the results obtained with Collins solution, presumably by preventing the loss of potassium (Collins, Hartley et al., id., and Collins Halasz et al., id.). For that reason, Collins solution had a high magnesium content.

However, the role of magnesium was later questioned by other authors, obtaining equally good or even better results with solutions with a low or no content of magnesium (Jensen, id.; Downes G, Hoffman R, Huang J, Belzer F O: Mechanism of action of washout solutions for kidney preservation. Transplantation 16:46, 1973; and Mieny C J, Myburgh J A, Smit J A: Liver preservation in the primate by simple cooling. In Lie T S, Gutgemann A, eds.: Liver Transplantation. Verlag Gerhard Witzstrock GmbH, Baden-Baden, 1974 pp. 145–148. The cited portions of these references are incorporated by reference herein.), and in a tissue slice model it was shown that the presence of $Mg^{2+}$ did not influence the loss of $K^+$ during hypothermia (Downes, et al., id.). For that reason, magnesium was taken away in the Euro—collins solution, which then was free from both calcium and magnesium. Then the attention was focused on the content of cell membrane impermeant solutes in Collins solution. Collins solution has a high content of glucose and sulfate, which are relatively impermeable in kidney cells. By balancing the osmotic pressure created by the intracellular cell membrane impermeable anions with cell membrane impermeable substances in the preservation solution, the development of hypothermia induced cell swelling during cold storage of the kidneys could be prevented.

Glucose is relatively impermeable to kidney cells but not to liver cells. The high content of glucose in Collins and Euro-collins solution effectively contracts the hypothermia induced cell edema in kidneys, but not in livers. For liver preservation, in another solution, named University of Wisconsin solution, glucose was taken away and instead raffinose and lactobionate were added. These two substances are also impermeable to cell membranes both in kidneys and livers. Now 24 hour preservation of the canine liver could be obtained (Jamieson N V, Sundberg R, Lindell S, Southard J H Belzer F O: A comparison of cold storage solutions for hepatic preservation using the isolated perfused rabbit liver, Cryobiology 25:300, 1988; Jamieson N V, Sundberg R, Lindell S, Claesson K, Moen J, Vreugdenhil P K, Wight D G D, Southard J H, Belzer F O: Preservation of the canine liver for 24–48 hours using simple cold storage with UW solution. Transplantation 46:517, 1988. These references are incorporated by reference herein.). Since 1988, University of Wisconsin solution has been the organ and tissue preservation solution most used in clinical transplantation. University of Wisconsin solution is free of calcium and has an intracellular electrolyte composition. It contains raffinose and lactobionate as cell membrane impermeable molecules to counteract the cold induced cell swelling, and it contains hydroxyetylstarch to create colloid osmotic pressure.

In an article published in 1981 (Nozick J H, Farnsworth P, Montefusco C M, Parsonnet V, Ruigrok T J C, Zimmerman A N E, Autogenous vein graft thrombosis following exposure to calcium-free solutions (Calcium paradox), J. Cardiovas. Surg., 22 166, 198 1), Nozick used an extracellular solution to irrigate and rinse external jugular veins in dogs before they were autotransplanted into the femoral artery. The veins were irrigated and kept in the extracellular solution for 45 minutes before transplantation. In one group, the irrigation solution contained calcium and another was without calcium. It was concluded that it was better to irrigate the veins with extracellular solution containing calcium. However, it must be noted that this study was not an organ preservation study where cold ischemic storage for an extended period was the goal. When Starzl tried to use Ringer's lactate which also contains calcium, he was not able to preserve canine livers for more than 2 hours. All the researchers making efforts to develop an organ preservation solution in the 80's, i.e. at the time of the Nozick article, knew that an organ had to be preserved based on principles far different from simply using extracellular solutions containing calcium. At that time it was dogma, not at all affected by the publication of the Nozick article, that an organ preservation solution should be free of calcium so that when the sodium potassium pump stopped due to the effects of hypothermia, no extracellular calcium could diffuse into the cells causing cell destruction.

It should also be noted that Nozick et al. only performed morphological studies, i.e. electron microscopic studies of the endothel anatomy, but no functional studies of the endothel, and more precisely, no studies of endothel dependent and independent relaxation, respectively, and also of the calcium influence on contraction and relaxation of the vascular smooth muscles. Thus the morphological study by Nozick et al. can in no way be correlated to the functional study by the present inventors, and it can not be concluded from the Nozick et al. study that the function of the endothel and smooth muscles is influenced by calcium in such an advantageous manner as found by the present inventors.

Extracellular solutions such as Ringer's lactate, Kreb's solution and an LPD ("low potassium dextran") solution, i.e. a so-called Perfadex solution, thus can preserve blood vessels for 2 hours at room temperature (20° C.). However, of these three solutions, only the LPD solution contains a colloidosmotically active substance, viz. dextran 40, a large sugar molecule of an average molecular weight of about 40,000 daltons. The colloidal osmotic pressure is that part of the osmotic pressure exerted by a solution that is due to dissolved colloids, i.e. the so-called "suction pressure" that protein molecules and other bigger molecules which cannot pass the capillary membrane exert so as to retain fluid in the capillaries. This LPD solution, which will be defined in more detail below, thus has a colloidal osmotic pressure which is slightly higher than that of normal plasma. In a series of studies, other scientists have demonstrated that dextran 40 is favourable for preventing thrombosis by covering the endothelium, which means that activated white blood corpuscles cannot get stuck with their receptors and thus invade and consequently destruct the vessel. In long-term preservation of blood vessels, for instance 36 hours, Ringer's lactate or Kreb's solution cannot preserve the blood vessel in a sufficiently satisfactory manner. However, the Perfadex solution tested gave good preservation for 36 hours.

In the remaining clinical organ transplantation today, two organ preservation solutions are thus prevalent, i.e. the so-called University of Wisconsin solution and the Euro-Collins solution. These solutions are so-called intracellular preservation solutions, i.e. they have a high potassium content, a low sodium content, and no calcium. The purpose of this composition is that the cells should be allowed to "swim" in an intracellular inactive environment. The applicant's research team has, however, after extensive studies demonstrated that in respect of blood vessels, the high potassium content of these intracellular solutions causes a violent vascular spasm. Therefore, there is no logic in using preservation solutions of intracellular electrolyte composition when storing vascular transplants.

In summary, then, it is important to appreciate the distinction between, on the one hand, an extracellular solution which is created for intravenous infusions of a dehydrated patient, and which is also used to irrigate and rinse tissues and wounds, and on the other hand, an organ and tissue preservation solution created for cold ischemic storage. As stated above, University of Wisconsin organ preservation solution is today the leading organ preservation solution used for clinical transplantation in the world. To preserve kidneys, livers and pancreas it is almost exclusively used by all transplant surgeons, and it is even more and more used in heart preservation. For lung preservation, the most used solution has been, and probably still is, Euro-collins solution. Both these solutions are calcium-free for the reasons earlier discussed. They have intracellular electrolyte compositions, cell impermeable molecules, and are buffered.

In heart surgery, a continuously increased use of so-called homotransplants, i.e. from one individual to another of the same species, has recently become common. This means that blood vessels are removed from recently deceased individuals, in most cases in institutes of forensic medicine, and after a short-term storage, these blood vessels are cryopreserved, i.e. they are stored in fluid nitrogen at low temperatures. In heart transplantations it is in many cases also possible to make use of the aortic root including the valve apparatus of the heart that are to be removed and discarded in any case. At present, this preparation is placed in a saline solution until it is being taken care of the next day to be cryopreserved.

In plastic surgery, the extent of microsurgical procedures increases, in which parts of organs, including blood vessels, are moved from one place in the body to another, i.e. autotransplantations. Also in this part of surgery, there is a need of a satisfactory preservation solution for the vascular system in the organs involved, such that when the organ is inserted, a perfect circulation of the blood can be established when the flow of blood is started.

A further problem, which has recently been discovered, is that in reperfusion of a transplanted organ or blood vessel, injuries to the cells may arise owing to detrimental free oxygen radicals within a few seconds up to some minutes after the implantation. Summing up, there is thus at present no quite satisfactory preservation solution available for organs and tissues or parts thereof from humans and animals, especially for blood vessels, which are to be transplanted or stored for some other purpose, for instance for medical studies. In these fields, there is thus a great global need of an improved preservation solution which does not have the drawbacks of existing preservation solutions and which preserve the original structures and functions of the organ, the tissue or parts thereof to a much greater extent and for a considerably longer period of time.

OBJECT OF THE INVENTION

An object of the present invention is to eliminate the above drawbacks of existing preservation solutions for organs and tissues or parts thereof from humans and animals.

This object is achieved by an improved preservation solution of the type mentioned by way of introduction, containing calcium, nitroglycerin and at least one colloidosmotically active substance. Further features are stated in the appended claims.

The present invention also relates to a method for preserving organs and tissues or parts thereof from humans and animals in the preservation solution and to methods for preserving endothelium-dependent relaxation factor function in organs, tissues and parts thereof, preserving the contractile function in contractile tissue and maintaining the integrity of vascular endothelium.

DESCRIPTION OF THE DRAWINGS

FIGS. 3–5 show the pulmonary vascular resistance, the mean pulmonary arterial pressure, and the blood flow, respectively, plotted against the time for a pig lung preservation experiment.

DESCRIPTION OF THE INVENTION

Figure 1:
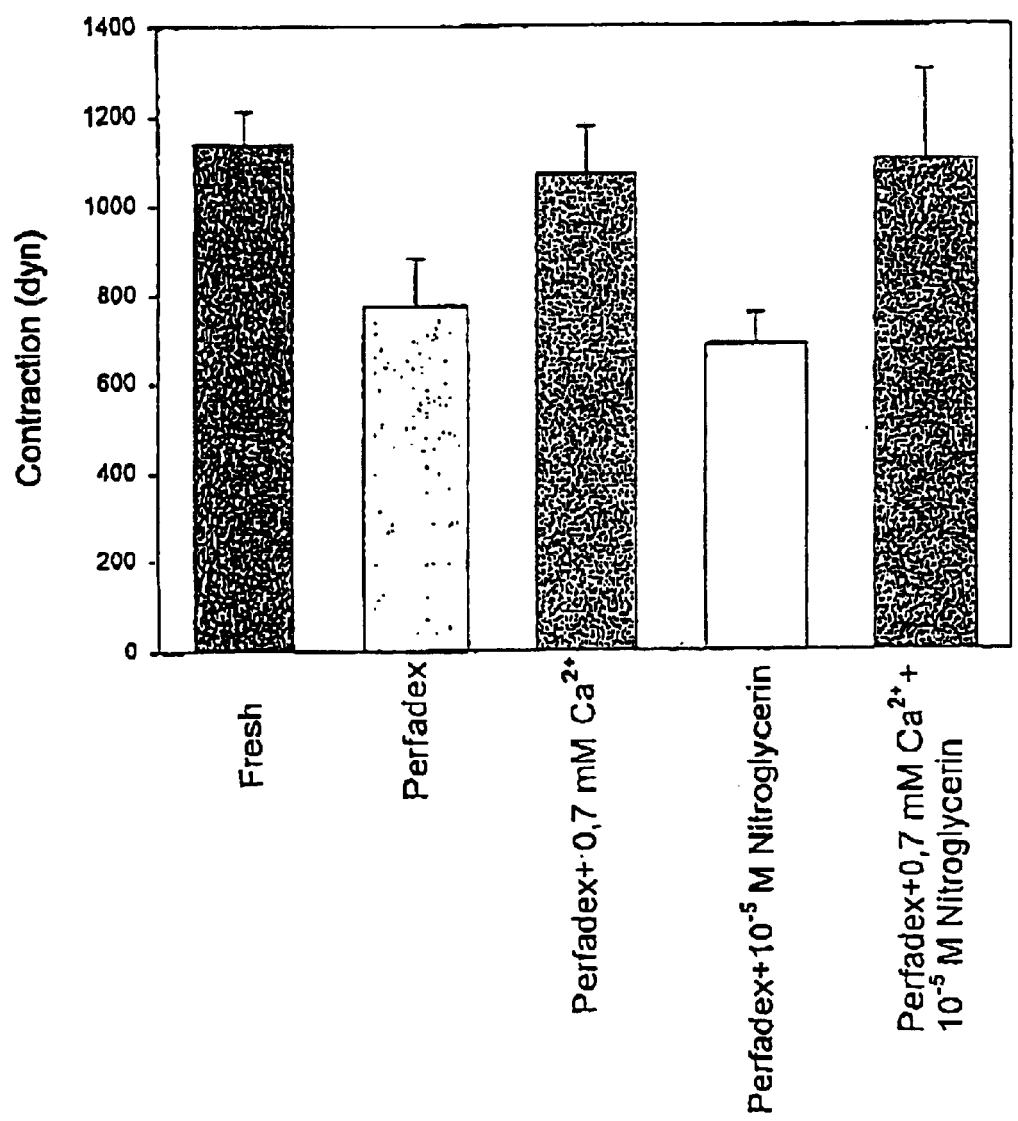
FIG. 1 shows comparative tests between preservation solutions containing the combination of calcium and nitroglycerin and these ingredients separately.
Figure 2B:
FIG. 2 shows the effect of calcium on muscle cells and endothelial cells in blood vessels.
Figure 2A:
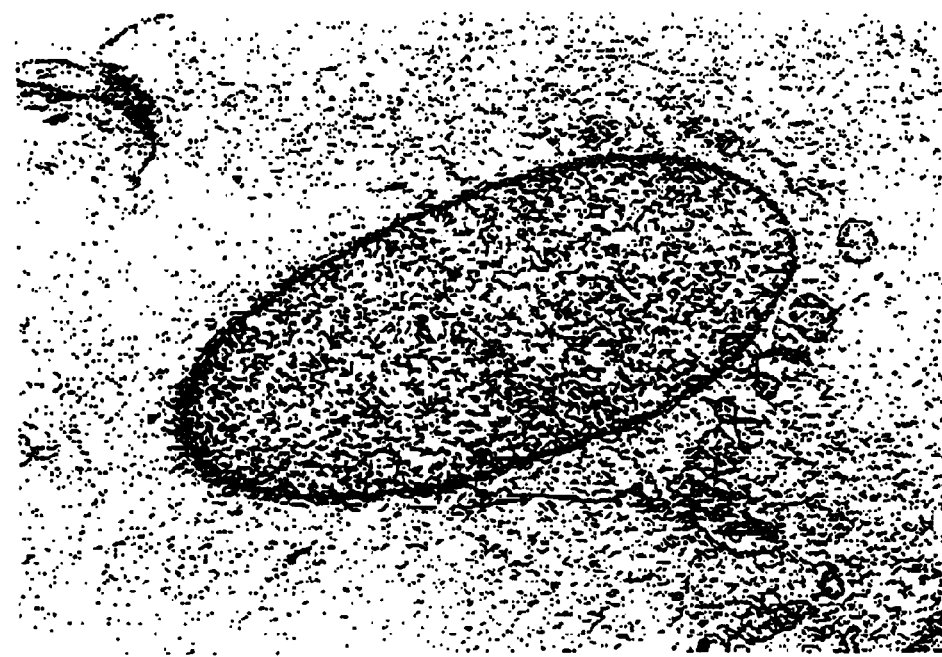
Figure 2D:
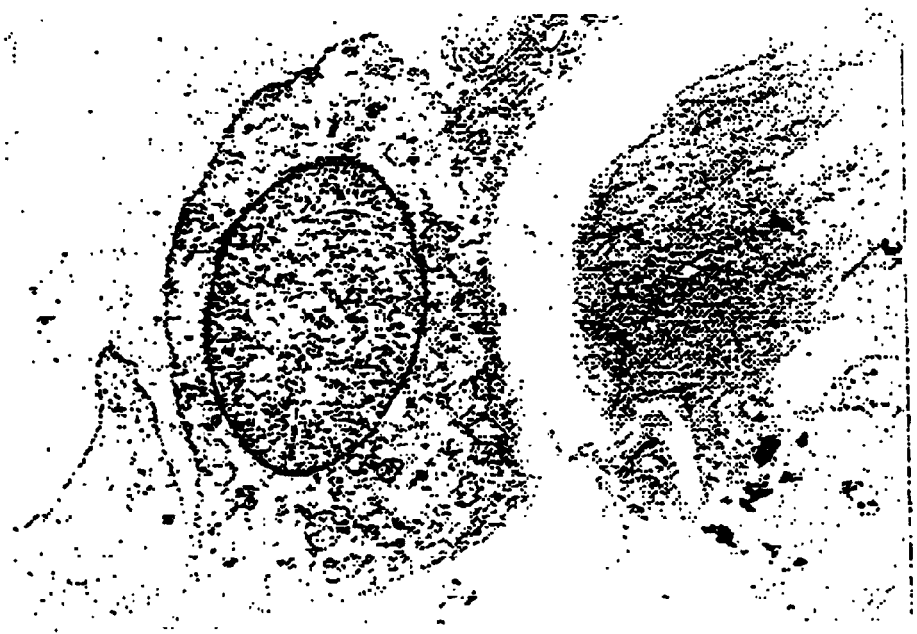
Figure 2C:
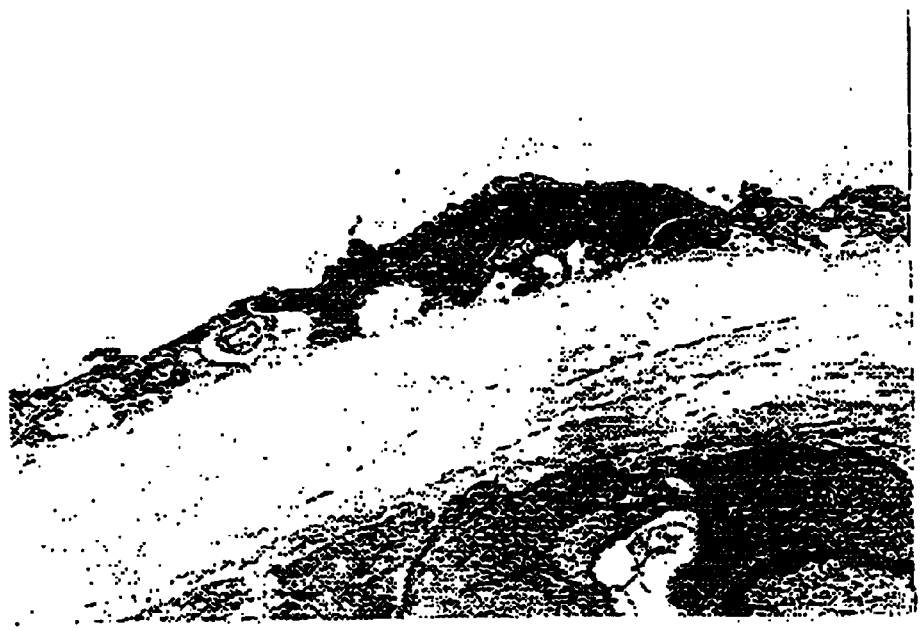

The applicant's research team has, after extensive studies and experiments, arrived at the surprising and seemingly contradictory result that calcium has a previously not shown potent function in long-term preservation of, above all, blood vessels, and can preserve the smooth muscle function in blood vessels for up to 36 hours.

It has for a long time been considered that calcium should not be present in preservation solutions for transplants. The reason for this is that in case of ischaemia, i.e. localized lack of oxygen in a tissue, the intracellular calcium concentration rises, and therefore one did not want to add further calcium so as to make this available to the cells. The applicant's research team has, however, carried out comparative studies showing that long-term preservation of blood vessels in calcium-free solutions is destructive to the blood vessel involved. The presence of calcium has proved to be necessary in the solution, among other things for maintaining the integrity of the vascular endothelium.

The vascular endothelium contains hydrocarbon chains which are bound to proteins in the cell membranes, and these constitute a so-called layer of glycocalyx. This is a thin layer of a mucous substance (composed of sugars) which is considered to enclose the cell membranes and which is important to the properties of immunity of the cell and makes the cell wall permeable. These hydrocarbon chains are bound together by, among other things, calcium. If the vascular endothelial cells are subjected to calcium-free solutions for a long time, a disintegration of the important layer of glycocalyx is assumed to take place, and the function of the endothelium thus cannot be perfect. Evidence of these discoveries has been obtained through electron microscope studies of cell membranes in blood vessels that have been stored in preservation solutions with and without calcium.

Moreover, the applicant's research team has found that the endothelial function in blood vessels can be maintained in a surprising manner by adding nitroglycerin to a preservation solution. Nitroglycerin probably constitutes a substrate for nitrogen oxide, NO, i.e. the endogenous substance that is produced in the endothelium and that constitutes one of the so-called endothelium-dependent relaxation factors (EDRF).

When preserving e.g. a blood vessel, it is of great importance to maintain as many biological functions as possible, inter alia, both the relaxation and the contraction activity. In blood vessels there are normally two types of relaxation, i.e. endothelial derived relaxation and relaxation directly of the vascular smooth muscles. In the improved preservation solution according to the present invention, the action of nitroglycerin is also, inter alia, to relax the smooth muscles, while at the same time the presence of calcium under influence of the nitroglycerin maintains the cell membrane integrity when it is cooled. When a blood vessel is cooled down to 4° C., which is the storage temperature used in organ preservation, the endothelium get rigid due to its high content of phospholipids. At the same time, the vascular smooth muscle will contract (cold induced contraction). The endothelium will then crack due to its rigidity. Nitroglycerin, which is a potent vasodilator, will prevent this cold induced spasm cracking the endothelium. Consequently, both types of vascular relaxation can be maintained intact. This synergistic effect is very important for the subsequent function of the transplanted blood vessel and is also much more pronounced than the corresponding effect obtained by use of either nitroglycerin or calcium separately. Further, there is also a synergistic effect in respect of the contraction of blood vessels. When nitroglycerin is present, strong vasocontraction is not possible.

In a comparative experiment with LPD solutions containing calcium and nitroglycerin, respectively, and an LPD solution containing both calcium and nitroglycerin, it has been found that a still better preservation of the EDRF function could be achieved in the presence of nitroglycerin in the solution.

As shown in FIG. 1, the combination of calcium and nitroglycerin in a transplantation solution for storing a rat aorta gives better results in respect of contraction than if the solution does not contain either calcium or nitroglycerin. The use of calcium in the absence of nitroglycerin in an improved preservation solution according to the present invention yields, in itself, a much better effect than that achieved by using prior art preservation solutions. Thus, in one embodiment of the present invention, the improved preservation solution defined above lacks nitroglycerin, i.e. comprises only calcium and at least one colloidosmotically active substance as main ingredients. However, in combination with nitroglycerin, a still better effect is obtained. Even if the effect of calcium and nitroglycerin in combination is not considerably higher than the effect of calcium in the absence of nitroglycerin, every improvement of the effect in this field is very important for the subsequent transplantation to be as successful as possible.

Morphological pictures concerning the satisfactory and unexpected effect of calcium are shown in FIG. 2. The pictures show, on the one hand, smooth muscular cells from blood vessels and, on the other hand, endothelial cells from blood vessels that have been stored for a long time with or without calcium. In the case of preservation without calcium (a: smooth muscular cell and c: endothelial cell), there appears an enormous swelling of the nuclei and the cytoplasm in both types of cells. In case of preservation with calcium, normal structures of the cells appear (b: smooth muscular cell and c: endothelial cell).

Nitroglycerin has also been found to have an important effect in the reperfision of the blood vessel or the organ after implantation. Cell injuries may in fact arise within a few seconds up to a minute or two after the implantation by the forming of free oxygen radicals. The nitroglycerin has a so-called scavenging effect on these radicals and must be present directly in the implantation operation to reduce this problem. This requirement is satisfied by the nitroglycerin being included, together with calcium, in the preservation solution according to the present invention, in which it also exerts its favourable combination effect on the endothelium.

The expression "colloidosmotically active substance" as used throughout the patent application concerns substances to which the capillary wall is impermeable. The impermeability can be caused by the size of the molecules compared to the fenestrations (holes) in the capillary wall and/or the electric charge of the molecules. Examples of such substances are a high molecular weight dextran, e.g. dextran 40 (40,000 Daltons), 60, 70 or higher, or plasma proteins, e.g. albumin, and different starches, e.g. hydroxy ethyl starch (HES).

The expression "substrate" as used throughout the patent application concerns certain molecules a cell requires for its metabolism. Examples are glucose, fructose, galactose, pyruvic acid, fatty acids, triglycerides, amino acids, and alcohols.

The expression "organs and tissues or parts thereof from humans and animals" as used throughout the patent application concerns, in its widest sense, any type of organ and tissue structure that has been obtained from animals and humans and that preferably can be transplanted to humans and animals by autotransplantation, syngeneic transplantation, allotransplantation and xenotransplantation (for instance organs from pig and monkey to humans). The preservation solution according to the invention is particularly suited for blood vessels or parts thereof and lungs. By the term "blood vessel" is thus meant veins, arteries and capillaries including the aortic root with valve apparatus and the pulmonary root with valve apparatus (so-called homografts). Extensive studies of the preservation of parts of the body other than blood vessels, lungs and kidneys have not yet been carried out, but there is at present nothing that indicates that such organs would be affected detrimentally by preservation in the solution according to the invention. However, for the preservation of hearts, specific concentrations of electrolytes in the preservation solution are necessary, which will be evident from the following.

The term "transplant" used throughout the patent application, also called graft, concerns organs and tissues or parts thereof according to the above definition that are to be transplanted in any of the manners as mentioned.

The term "improved preservation solution" used throughout the patent application concerns a preservation solution or liquid in which the above-mentioned organs and tissues or parts thereof are to be stored, for instance before transplantation for a long time, e.g. up to 36 hours or more (some functions have been preserved up to one week), while completely maintaining all of the structural and functional characteristics of the organs, tissues or parts thereof. The improved preservation solution also has to be hyperosmolar, due to the presence of cell membrane impermeable molecules, e.g. dextran 1, raffinose, and lactobionate, thereby preventing cell oedema when lowering the organ temperature. It should also contain large molecules which give the solution a colloidosmotic pressure, thereby making it possible to perfuse organs without creation of tissue oedema. Also, it has to contain other beneficial substances with a view to preventing the harmful effects of ischemic metabolites arising during the preservation. Thus, it is of great importance to distinguish between preservation solutions and wash, irrigation and infusion solutions. The latter are sometimes wrongly referred to as preservation solutions in the literature.

The improved preservation solution is, as mentioned above, also intended to be used for preservation without subsequent transplantation, for instance for different kinds of examinations and studies.

In a preferred embodiment, the inventive improved preservation solution contains, in addition to calcium and nitroglycerin, also about 1–15, preferably 5–15, and most preferably about 7–12% by weight low-molecular dextran having an average molecular weight of about 1,000 daltons (e.g. dextran 1), about 3–8% by weight high-molecular dextran (e.g. dextran 40, dextran 60, dextran 70 or higher, such as dextran 120), about 0.1–2.6% glucose, buffer (e.g. phosphate, THAM or hydrogen carbonate), about 4–25 mM potassium, about 1–16 mM magnesium, about 50–150 mM sodium and about 50–150 mM chloride. 5% by weight dextran 1 theoretically results in an osmolarity of about 50 milliosmoles. When this is added to the solution, the concentration of electrolytes (for instance sodium and chlorine) must be reduced so as to prevent the solution from becoming too hyperosmolar.

In a further preferred embodiment of the invention, the preservation solution contains, in addition to calcium and nitroglycerin, also a so-called Perfadex solution, which is a commercially available preservation solution. The Perfadex solution contains 50 g/l dextran 40 (colloidosmotically active substance) of an average molecular weight of 40,000 daltons, 5 mM glucose, phosphate buffer which gives a phosphate content of 0.8 mM, 6 mM potassium, 0.8 mM magnesium, 138 mM sodium, 142 mM chlorine and 0.8 mM sulphate, and an addition of THAM buffer such that a pH of about 7.4 is obtained.

All the above-mentioned contents are based on the final improved preservation solution.

Regarding the preservation of hearts in the preservation solution according to the present invention, the potassium content must be increased to about 16–25 mM, preferably to 23 mM, and the magnesium concentration to about 12–16 mM, preferably 15–16 mM. The concentration of sodium then decreases such that the osmolarity of the solution does not exceed about 340 milliosmoles per liter. When storing other organs and tissues, the potassium concentration usually is about 4–6 mM and the magnesium concentration usually is about 1–4 mM, based on the final preservation solution.

The Perfadex solution, which is one type of the above-mentioned LPD solution, has previously been found to function as a long-term preservation liquid for transplants, especially kidneys, before transplantation. Perfadex is a preservation solution with a sodium and potassium concentration which is about the same as that in plasma. The phosphate buffer and the THAM buffer therein have a great buffering capacity and give the solution a pH of 7.4. The glucose functions as substrate in the metabolism, and dextran 40 gives the solution a colloidosmotic pressure about double that of normal plasma, as well as functioning as an oxygen free radical scavenger.

All greater dextran molecules, such as from dextran 40 and upwards, suffer from the drawback that when administered, they may cause anaphylactic reactions. Only small amounts of these molecules suffice to cause these fatal reactions. Low-molecular dextran, for instance dextran 1, also called Promiten, is therefore administered to patients in these contexts with a view to preventing this reaction. The risk of such anaphylactic reactions is eliminated by the preservation solution according to the invention containing low-molecular dextran.

However, the Perfadex solution does not in itself have satisfactory properties in respect of maintaining the smooth muscle function and the endothelial function in blood vessels. The addition of calcium and nitroglycerin to Perfadex results, however, in a significant improvement of the properties of the preservation solution in respect of maintaining these functions in long-term preservation.

Also, even though conventional preservation solutions are able to preserve organs and tissues for a short time in a non-completely although satisfactory way, the improved preservation solution according to the present invention is superior also for short term preservation.

In the improved preservation solution according to the present invention, calcium is present in a concentration of 0.3–1.5 mM, preferably about 1.1 mM, based on the final improved preservation solution. Calcium can be added separately during the preparation of the preservation solution in the form of a solution, for instance an aqueous solution, of calcium or is added in solid state, such as a salt, preferably $CaCl_2$, the negatively charged ion in the salt being such as not to detrimentally affect the properties of the preservation solution.

In the improved preservation solution according to the present invention, nitroglycerin is present in a concentration of $10^{-4}$–$10^{-7}$ M, preferably about $10^{-5}$–$10^{-6}$ M, based on the final solution. Nitroglycerin can be added separately during the preparation of the solution, either in the form of a solution or in solid state. A usable alternative to nitroglycerin is a preparation called Nipride, whose active ingredient is nitroprusside, e.g. in the form of nitroprusside sodium. Other alternatives to nitroglycerin include papaverine, nifedipine, and other vasodilating substances.

According to the present invention, heparin can optionally be added to the improved preservation solution in a concentration of 1–12 IE/ml, preferably 10 IE/ml, based on the final improved preservation solution. Heparin is used for the purpose of preventing coagulants from forming on the inside of the vascular transplant in case it should be impossible to wash away all blood when removing the organ. Moreover, extensive studies have shown that heparin is not toxic to the endothelial function. As an alternative to common heparin, a so-called low-molecular heparin, preferably fragmin (Dalteparin), can be used.

Antibiotics can also be added to the preservation solution according to the present invention. An example of an effective antibiotic is benzyl penicillin in a concentration of about 120 mg/l.

All ingredients in the improved preservation solution according to the invention, also the optional ones, can be added separately and in any order whatever. In a preferred embodiment, calcium, nitroglycerin and optionally heparin and/or an antibiotic are added to a ready-mixed solution, e.g. Perfadex, containing the remaining ingredients for producing the preservation solution.

When used, the pH of the preservation solution should be kept in a range of about 7.4–7.6. Any buffer whatever that yields the necessary pH and that does not detrimentally affect the function of the preservation solution can be used.

The inventive improved preservation solution is ideal for its purposes by containing the following ingredients and having the following functions:
1) extracellular composition of electrolytes including calcium, i.e., no electrolytes causing vascular spasm,
2) an effective buffer system that can keep a pH of about 7.4–7.6,
3) colloidosmotically active substances (e.g. highmolecular dextran), which can give the solution a colloidosmotic pressure corresponding to that of plasma, i.e. 25 mm Hg or higher, when necessary,
4) a low-molecular, but cell-membrane-impermeable substance (e.g. 5–15% dextran 1), which can give the solution an osmolarity in the range of 50–150 milliosmoles,
5) an efficiently vasodilating substance, e.g. nitroglycerin, nitroprusside, papaverine or nifedipine,
6) a coagel-inhibiting additive, e.g. heparin or fragmin (Dalteparin),
7) glucose or another substrate for the metabolism during the term of preservation,
8) optionally an antibiotic which is not tissue-toxic in long-term preservation, and
9) increased potassium and magnesium contents for the storing of hearts.

In relation to prior art preservation solutions for organs and/or tissues which, for instance, are to be transplanted, the improved preservation solution according to the present invention thus contains, besides the colloidosmotically active substance(s), two new active ingredients which each separately, and especially in combination, in a surprising manner favourably affect the organs and/or tissues during preservation. The effects of these two ingredients, i.e. calcium and nitroglycerin, are not previously known in this context, and make the inventive preservation solution a universally promising preparation.

The inventive improved preservation solution can be held in any conventional container that is suitable in the art.

The invention further relates to a method for preserving organs and tissues or parts thereof from humans and animals in an improved preservation solution according to the invention, the organ and tissue or parts thereof being flushed with and immersed in the improved preservation solution, and the temperature of the preservation solution being adjusted in the range of 4–24° C. for a time of at most about 2 hours for short-term preservation, or at a temperature in the range of 0.5–12° C., preferably 2–8° C. for at most 36 hours for long-term preservation.

The organ, tissue or parts thereof from humans and animals that have been removed from the donor involved should, if possible, be flushed in situ and/or as soon as possible after that be placed in the improved preservation solution for minimizing detrimental effects, if any.

The optimal storing temperature for the inventive preservation solution is completely dependent on the planned storing time. In case of short-term preservation of blood vessels, i.e. up to 2 hours, the optimal temperature is room temperature. Too low temperatures are not optimal for the endothelium, but it resists down to 4° C. fairly well. After about 2 hours reperfusion in vivo after the transplant has been fixed, the endothelial function has been restored completely. When decreasing the temperature to 1 ° C., the function of the endothelium will be deteriorated and is not restored after 2 hours, but after 24 hours. For long-term preservation, it is thus a requirement that the temperature be low. 0.5–12° C., preferably 2–8° C., and more preferably 4° C., has been found to be most advantageous. Different organs have a specific optimal storing temperature when stored up to 36 hours.

In the EU alone, having more than 400 million inhabitants, for instance more than about 300,000 coronary bypass operations are performed each year, and in Sweden about 7,000 a year. In the USA, this type of operation is the most common operation in all categories. An improved preservation solution according to the present invention should, for instance, also be available for taking care of homotransplants in institutes of forensic medicine. As mentioned above, there is also a great need of storing blood vessels in a satisfactory preservation solution until they can be cryopreserved the next working day. In peripheral vascular surgery and in plastic and reconstruction surgery, there is also a need of having such a preservation solution.

EXPERIMENTS

36 Hour Lung Preservation Using the Inventive Improved Preservation Solution as Preservation Medium The animal used was a 60 kg Swedish native breed pig.

The donor pig was anesthetized and the thorax was opened via a median sternotomy. 1 mg nitroglycerin was given intravenously. One minute later, the pulmonary artery was flushed with Perfadex (4° C.) containing 1 mg/L nitroglycerin 1 mg/L and 1.1 mmol/L calcium. Thirty mL preservation solution was given per kg body weight, and the perfusion pressure was kept at 10 cm $H_2O$. The animal was ventilated with an inspired oxygen fraction of 0.5 ($FiO_2$=50%) during the perfusion. When the perfusion was fulfilled, the trachea was clamped with the lungs in a semi-inflated state (during expiration). The heart-lung block was excised and placed in an identical perfusion solution in a refrigerator for 36 hours.

The recipient, which had a blood group identical with that of the donor, was anesthetized. The left lung was removed and the left donor lung transplanted. Reperfusion was started. When the blood flow through the transplanted lung had reached the normal level, which is around 2 L/min (in pigs the left lung represents 35% of the total lung volume, i.e. 35% of 5 L), a right pneumonectomy was performed, thereby making the animal totally dependent on the transplanted lung. This means that the whole cardiac output goes through the transplanted lung. The animal was totally recorded during 25 hours.

Figure 3:
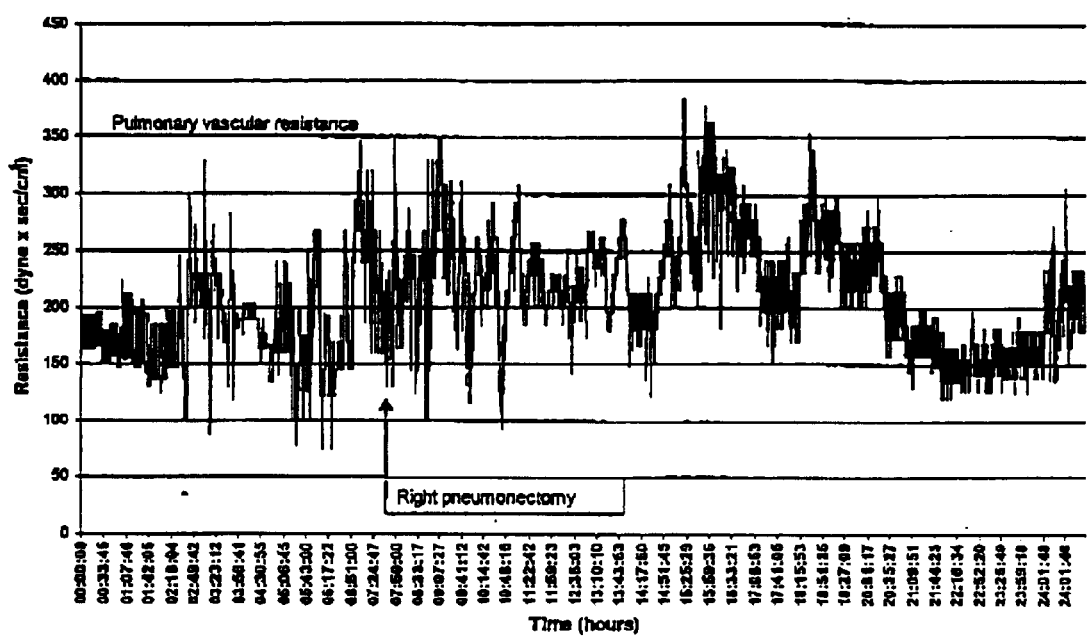

The pulmonary vascular resistance (PVR) was around 200 dynexsec/$cm^5$ (FIG. 3). This is a normal level for pigs. In a previous paper entitled "Safe Lung Preservation for Twenty-Four Hours With Perfadex" (Ann Thorac Surg 1994;57:450–457), which is incorporated by reference in its entirety, we describe the results of similar experiments, but using Perfadex without nitroglycerin and calcium, and compared that group with a control group where only right pneumonectomy was done (no transplantation). In the control group, the PVR was around 300 dynexsec/$cm^5$, and in the transplanted group it was around 500 dynexsec/$cm^5$ throughout the 24 hours of postoperative recording.

Figure 4:
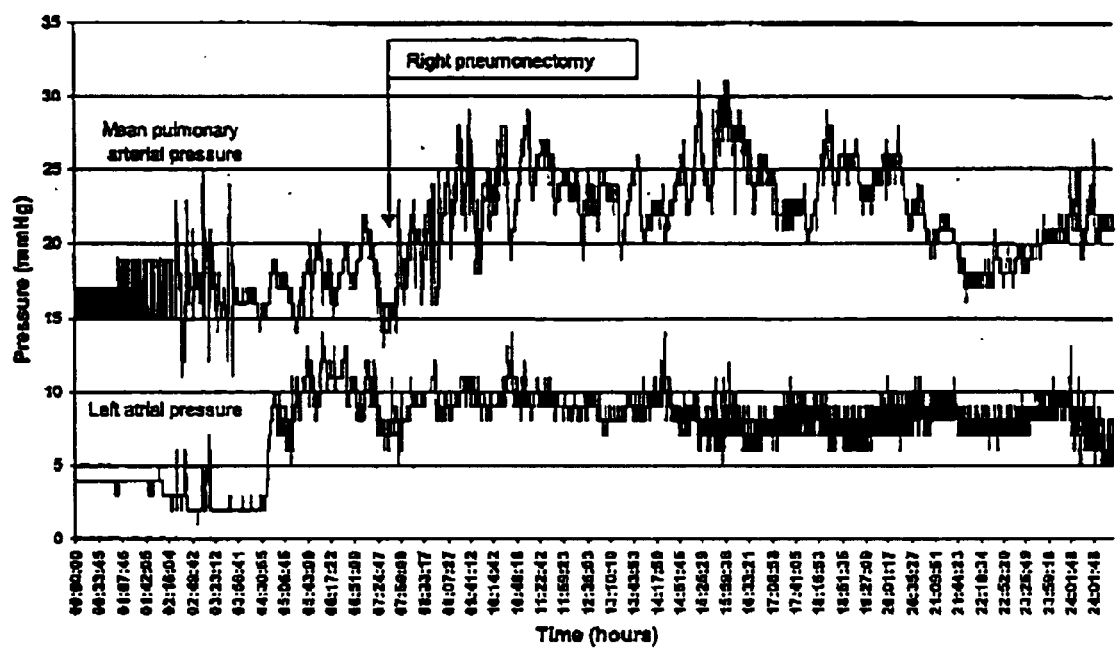

In the present experiment the mean pulmonary arterial pressure (MPAP) was between 15 and 20 mm Hg before the right pneumonectomy was done, and on average about 25 mm Hg when the pig was living only with the transplanted lung (FIG. 4). In the above-mentioned experiments the MPAP was around 25 mm Hg in the control group and 30 mm Hg in the transplanted group.

The left atrial pressure (LAP) was 10 mm Hg or lower in the present experiment, as well as in both groups of the earlier experiments (FIG. 4).

The blood flow was measured with an ultrasonic based flow probe (Transonic Systems Inc.) in the pulmonary artery of the transplanted lung, and cardiac output measured using the Swan-Ganz technique (FIG. 5). After reperfusion of transplanted lung, the flow slowly increased to about 1 L/min during the first hour. After 6 hours, normal blood flow (about 2 L/min) was reached in the transplanted lung. After the right pneumonectomy the flow increased to 4 to 5 L/min. The cardiac output measurements obtained with the Swan-Ganz technique showed that the flow was 1.3 times higher with this methodology. This discrepancy between two such different measuring techniques is acceptable.

The lung function as measured by the ability of oxygenating the blood was normal; 18 hour after the right pneumonectomy (the end of the experiment) the $pO_2$ was 76 kPa with a $FiO_2$ of 100%, 39 kPa with a $FiO_2$ of 50% and 11 kPa with air ($FiO_2$ of 21%). These values are to be compared to the results from the former above-mentioned experiments where the PaO2 was 60 kPa, 33 kPa and 14 kPa, respectively, in the control group, and 43 kPa, 22 kPa and 7 kPa, respectively, in the transplanted group.

Conclusively, by the addition of nitroglycerin and calcium to Perfadex, the results of lung transplantation are dramatically improved. Other experiments with Perfadex containing only calcium but no nitroglycerin showed normal blood gas values but the pulmonary vascular resistance was higher. During the 24 hour post transplant recording, PVR was between 300 and 500 dynexsec/$cm^5$.

I claim:

1. A preservation solution for organs and tissues or parts thereof from humans and animals containing endothelium, comprising:

calcium ion, nitroglycerin, about 1–15% by weight low-molecular dextran having an average molecular weight of about 1,000 daltons, about 3–8% by weight high-molecular dextran having an average molecular weight of 40,000–120,000 daltons as a colloidosmotically active substance, about 0.1–2.6% glucose as a substrate, buffer, about 4–25 mM potassium ions, about 1–16 mM magnesium ions, about 50–150 mM sodium ions, and about 50–150 mM chloride ions, wherein the amounts are based on the final volume of the preservation solution.

2. A preservation solution for organs and tissues or parts thereof from humans and animals containing endothelium, comprising:

calcium ion, at least one colloidosmotically active substance, and nitroglycerin, wherein said solution comprises 50 g/l dextran 40 having a molecular weight of about 40,000 daltons as said colloidosmotically active substance, 5 mM glucose as substrate, 0.8 mM phosphate buffer, 6 mM potassium ions, 0.8 mM magnesium ions, 138 mM sodium ions, 142 mM chlorine ions, 10.8 mM sulphate ions, and THAM buffer, based on the final volume of the preservation solution.

3. The preservation solution according to claim 1, wherein the concentration of potassium ions is about 16–25 mM, and the concentration of magnesium ions is about 12–16 mM, based on the final volume of the preservation solution.

4. A method for preserving organs and tissues or parts thereof from humans and animals, comprising:

flushing an organ or a tissue with, and immersing in, the preservation solution according to claim 1, and storing said solution containing said organ or tissue at a temperature of 0.5–120° C. for at most 36 hours for long-term preservation, or at a temperature of about 4–24° C. for at most 2 hours for short-term preservation.

5. The method of preserving organs and tissues or parts thereof from humans or animals according to claim 4, wherein said tissue comprises blood vessels or parts thereof.

6. The method of preserving organs and tissues or parts thereof from humans or animals according to claim 4, wherein said tissue is vena saphena magna or parts thereof.

7. The method of preserving organs and tissues or parts thereof from humans or animals according to claim 4, wherein said organs and tissues comprise lungs.

8. A method of preserving endothelium-dependent relaxation factor function in organs, tissues and parts thereof, comprising storing said organs, tissues and parts thereof in the preservation solution according to claim 1.

9. A method of preserving contractile function in contractile tissue, comprising storing the contractile tissue in the preservation solution according to claim 1.

10. A method of preserving contractile function in contractile tissue, comprising storing the contractile tissue in the preservation solution according to claim 1, wherein:

nitroglycerin is present in an amount of about $10^{-4}14\ 10^{-4}$ M; and calcium ion is present in an amount of about 0.3–1.5 mM, based on the final volume of preservation solution.

11. A method for maintaining the integrity of vascular endothelium, comprising:

placing said organs, tissues and parts thereof into the preservation solution according to claim 1.

12. A method for preserving vascular endothelium, comprising:

storing a contractile tissue in the preservation solution according to claim 1, wherein nitroglycerin is present in an amount of about $10^{-4}$–$10^{-4}$ M; and calcium ion is present in an amount of about 0.3–1.5 mM, based on the final volume of preservation solution.

13. A method for preserving organs and tissues or parts thereof from humans and animals, comprising:

flushing an organ or a tissue with the preservation solution according to claim 1, immersing the organ or the tissue in the preservation solution, and storing the preservation solution containing the organ or the tissue for 36 hours or more at 0.5–12° C.

14. A method for preserving organs and tissues or parts thereof from humans and animals, comprising:

flushing an organ or a tissue with, and immersing in, the preservation solution according to claim 1, and storing said solution containing said organ or tissue at a temperature of 2–8° C., for at most 36 hours for long-term preservation, or at a temperature of about 4–24° C. for at most 2 hours for short-term preservation.

\* \* \* \* \*

UNITED STATES PATENT AND TRADEMARK OFFICE
CERTIFICATE OF CORRECTION

PATENT NO. : 6,794,124 B2
DATED : September 21, 2004
INVENTOR(S) : Stig Steen

It is certified that error appears in the above-identified patent and that said Letters Patent is hereby corrected as shown below:

Title page,
Item [73], Assignee, change "FACTHOR, STIFTELSEN" to -- XENODEVICE AKTIEBOLAG --.

Signed and Sealed this

Tenth Day of January, 2006

JON W. DUDAS
*Director of the United States Patent and Trademark Office*